United States Patent [19]

Eggers et al.

[11] Patent Number: 5,366,443
[45] Date of Patent: Nov. 22, 1994

[54] METHOD AND APPARATUS FOR ADVANCING CATHETERS THROUGH OCCLUDED BODY LUMENS

[75] Inventors: Philip E. Eggers, Dublin, Ohio; Hira V. Thapliyal, Mountain View, Calif.

[73] Assignee: Thapliyal and Eggers Partners, Mountain View, Calif.

[21] Appl. No.: 958,977

[22] Filed: Oct. 9, 1992

Related U.S. Application Data

[63] Continuation-in-part of Ser. No. 817,575, Jan. 7, 1992, abandoned.

[51] Int. Cl.⁵ .............................................. A61B 1/00
[52] U.S. Cl. .................................................... 604/114
[58] Field of Search ............... 604/113, 114, 22, 41; 606/27-32, 35, 38, 41; 128/401, 402

[56] References Cited

U.S. PATENT DOCUMENTS

| | | | |
|---|---|---|---|
| 2,050,904 | 8/1936 | Trice | 606/29 |
| 3,460,539 | 8/1968 | Anhalt, Sr. | 128/303 |
| 3,769,984 | 11/1973 | Muench | 128/404 |
| 4,011,872 | 3/1977 | Komiya | 128/303 |
| 4,532,924 | 8/1985 | Auth et al. | 128/303 |
| 4,643,186 | 2/1987 | Rosen et al. | 128/303 |
| 4,654,024 | 3/1987 | Crittenden et al. | |
| 4,660,571 | 4/1987 | Hess et al. | 128/784 |
| 4,672,962 | 6/1987 | Hershenson | 128/303 |
| 4,682,596 | 7/1987 | Bales et al. | 128/303 |
| 4,699,157 | 10/1987 | Shonk | 128/786 |
| 4,709,698 | 12/1987 | Johnston et al. | |
| 4,754,752 | 7/1988 | Ginsburg et al. | |
| 4,765,331 | 8/1988 | Petruzzi et al. | 128/303 |
| 4,785,823 | 11/1988 | Eggers et al. | 128/692 |
| 4,796,622 | 1/1989 | Lu et al. | |
| 4,857,046 | 8/1989 | Stevens et al. | |
| 4,955,377 | 9/1990 | Lennox et al. | 128/401 |
| 4,976,711 | 12/1990 | Parins et al. | 606/48 |
| 4,998,933 | 3/1991 | Eggers et al. | |
| 5,057,105 | 10/1991 | Malone et al. | 606/28 |

FOREIGN PATENT DOCUMENTS

0182689  5/1986  European Pat. Off.
WO90/07303  7/1990  WIPO .

*Primary Examiner*—John D. Yasko
*Assistant Examiner*—Manuel Mendez
*Attorney, Agent, or Firm*—Townsend and Townsend Khourie and Crew

[57] ABSTRACT

A catheter comprises a catheter body having a proximal end, a distal end, and an electrode array disposed near the distal end. The electrode array includes a plurality of isolated electrode terminals. The electrode array and a common electrode are connected to a high frequency power supply, and the common electrode may be located on the catheter, may be secured separately to a patient's skin, or may be formed as part of a movable guidewire. By contacting the electrode array against a target location in the patient's body, the target location may be selectively heated, with current density being contacted at the points of contact between the electrode terminals and the tissue or stenotic material. For example, by positioning the common electrode within a stenotic region and contacting a leading surface of the stenotic region with the electrode array, the stenotic material can be heated by applying a high frequency voltage between the electrode array and the common electrode. The stenotic region can thus be recanalized by advancing the distal end of the catheter body through the heated stenotic material.

44 Claims, 10 Drawing Sheets

METHOD AND APPARATUS FOR ADVANCING CATHETERS THROUGH OCCLUDED BODY LUMENS

The present application is a continuation-in-part of application Ser. No. 07/817,575, filed on Jan. 7, 1992 now abandoned, the full disclosure of which is incorporated herein by reference.

BACKGROUND OF THE INVENTION

1. Field of the Invention

The present invention relates generally to the construction and use of catheters for interventional and diagnostic procedures. In particular, the present invention relates to methods and apparatus for advancing catheters through restrictions and occlusions within body lumens and cavities.

Atherosclerosis is a form of arteriosclerosis which is characterized by irregularly distributed deposits on the walls of a patient's arteries. Such deposits frequently fibrose and calcify over time, seriously compromising the patient's health.

A number of catheter-based approaches have been developed for diagnosing and treating atherosclerosis and other forms of arteriosclerosis. The most common interventional technique for treating atherosclerosis is balloon angioplasty where a balloon-tipped catheter is introduced to the vascular system, and the balloon expanded within a region of stenosis. Other interventional techniques include atherectomy, where, for example, a catheter having a cup-shaped rotating cutter is introduced to the vascular system and used to severe and capture at least a portion of the stenotic material. Other interventional techniques include laser ablation, mechanical abrasion, chemical dissolution, and the like. Catheter-based diagnostic techniques include ultrasonic imaging where an ultrasonic transducer disposed at the distal end of a vascular catheter is introduced to the region of stenosis.

With most of these techniques, it is necessary to advance the distal end of the catheter at least partly through the stenosed region before the interventional or diagnostic procedure can be commenced. While such initial advancement is often not a problem, it can be very problematic when the occlusion is severe and little or no lumen remains to receive the catheter. Under such circumstances, it is necessary to at least partly recanalize the occlusion before the catheter procedure can begin.

A number of methods for recanalizing severe occlusions have been proposed, including the use of hot-tipped catheters, laser catheters, and drill-tipped catheters. In general, these approaches rely on very aggressive treatment of the stenotic material to open up a passage, where such aggressive techniques can expose the blood vessel wall to significant injury, for example, vessel perforation. The risk of injury is exacerbated by the unconstrained path which the catheter can follow.

An improved technique for advancing an angioplasty catheter into and optionally through a severe occlusions is described in U.S. Pat. No. 4,998,933 (the entire disclosure of which is hereby incorporated herein by reference), which has common inventorship with the present application. A first electrode is disposed at or near the distal tip of the angioplasty catheter and a second electrode is provided on an electrically conductive guidewire. After the guidewire is at least partly advanced into a stenotic material, a high frequency voltage can be applied between the guidewire electrode and the catheter tip electrode in order to generate heat within the stenotic material lying between said electrodes. As the stenotic material is heated, it is softened, thereby allowing easier advancement of the angioplasty catheter.

Although a substantial improvement in the art, the catheter described in U.S. Pat. No. 4,998,933 can cause unwanted shorting of electrical energy by the blood and blood vessel wall during the application of the high frequency voltage. The catheter employs a single discrete electrode at its distal tip. So long as the tip electrode fully contacts the stenotic material, the induced heat will be substantially limited to the stenotic material. If a portion (or all) of the electrode is exposed to the blood vessel wall and/or blood, however, current will begin to flow through the blood vessel tissue and/or blood, causing the undesired shorting of electrical current. Moreover, since both the blood vessel wall and the blood have higher electrical conductivities than the stenotic material, they will carry the current in preference to the stenotic material.

For these reasons, it would be desirable to provide improved apparatus and methods for advancing vascular catheters past severe occlusions in blood vessels and other body lumens. In particular, it would be desirable to provide improved catheters of the type described in U.S. Pat. No. 4,998,933, where the catheter more selectively heats the atheromatous material. It would be further desirable if such catheters were able to discriminate between the atheromatous mass and the blood vessel wall (preferentially heating and ablating the former) so that the catheter would selectively pass through the atheroma as the catheter is advanced through the lumen of the blood vessel. The catheters and methods of the present invention should be compatible with a wide variety of interventional and diagnostic devices, particularly being compatible with angioplasty catheters.

2. Description of the Background Art

U.S. Pat. No. 4,998,933, is described above. European Patent Publication 182,689 and U.S. Pat. No. 4,754,752 describe angioplasty balloon catheters having means for internally heating the balloons. A "hot tip" catheter having a metal tip heated by a laser is described in Cumberland et al. (1986) Lancet i: 1457-1459. U.S. Pat. No. 4,654,024, describes a catheter having an electrically heated tip for melting atheroma. U.S. Pat. No. 4,796,622, describes a catheter having a tip which is heated by an exothermic reaction. A catheter having a high speed rotating abrasive element at its distal tip is described in U.S. Pat. No. 4,857,046. U.S. Pat. No. 4,709,698, describes the placement of electrode pairs on the surface of a dilatation balloon to heat atheroma as the balloon is expanded.

SUMMARY OF THE INVENTION

The present invention provides apparatus and methods for localized heating of target locations within a patient's body, such as atheromatous mass in blood vessels, tissue, and the like. The method and apparatus are particularly useful for advancing a catheter through an occluded region in a blood vessel or other body lumen, more particularly through stenotic regions in blood vessels which are fully or almost fully occluded with stenotic material. Catheter apparatus according to the present invention include a catheter body having a proximal end, a distal end, and an electrode array disposed near the distal end. The electrode array includes a plurality of isolated electrode terminals typically forming the distal tip of the catheter. A common electrode is provided and contacted with the patient's body to complete an electrically conductive path with the electrode array. The common electrode may be disposed on the catheter body proximally of the electrode array, or may be disposed distally of the electrode array, typically on or as part of a movable guidewire. As a third alternative, the common electrode may be provided as a discrete member which can be attached externally to the patient's skin. In each case, heating of the stenotic or other occluding material or high resistance tissue can be achieved by contacting the electrode array with the target location, e.g., a leading portion of the stenotic material. By then applying high frequency voltage between the electrode array and the common electrode, heating of the target location will result.

According to a particular aspect of the present invention, heating is directed primarily to the target location by limiting the current flow through each electrode terminal in the electrode array. In this way, more power is applied to the high resistance (low conductivity) tissue or stenotic material relative to the low resistance (high conductivity) blood and blood vessel wall. Current flow may be limited by active or passive devices, with an exemplary system employing a plurality of current limiting resistors, with at least one current limiting resistor in series with each electrode terminal.

The catheter of the present invention may be used alone in order to heat a target location e.g., to recanalize a stenotic region within a blood vessel. Optionally, the catheter may be used in combination with other interventional or diagnostic devices in order to provide a multiple step treatment and/or diagnostic procedure. In particular, it will be possible to provide the electrode array of the present invention in combination with or at the distal end of catheters which employ other interventional and/or diagnostic elements, such as dilatation balloons, lasers, ultrasonic transducers, and the like. By employing catheters having such additional capabilities, the need to exchange catheters is reduced or eliminated.

A particular advantage of catheters constructed in accordance with the principles of the present invention is that they can be "self-guiding" when introduced through a blood vessel. Since the electrode array heats atheromatous material in preference to the blood vessel wall, the catheter can be advanced without substantial concern over damage to the blood vessel wall. That is, the path of the catheter will be preferentially through the atheroma, necessarily limiting damage to the blood vessel wall.

The catheter of the present invention will preferably include a temperature measuring or sensing element near its distal tip, preferably within the electrode array, in order to measure the temperature at the interface between the electrode array and the tissue or stenotic material being treated. More preferably, a plurality of temperature measuring elements will be distributed through the electrode array in order to determine the temperature profile of the interface. Temperature information obtained from the temperature measuring elements can be used to control the power output to the electrodes in order to control the temperature of the stenotic material within a desired range.

DESCRIPTION OF THE PREFERRED EMBODIMENT

This invention provides a method and apparatus for selectively heating a target location within a patient's body, such as solid tissue, a body lumen, or the like, particularly including atheromatous material which partially or fully occludes a blood vessel or other body lumen. In addition to blood vessels, body lumens which may be treated by the method and apparatus of the present invention include the urinary tract (which for example may be occluded by an enlarged prostrate in males), the fallopian tubes (which may be occluded and cause infertility), and the like. For convenience, the remaining disclosure will be directed specifically at the treatment of blood vessels but it will be appreciated that the apparatus and methods can be applied equally well to other body lumens and passages.

The stenotic material in blood vessels will be atheroma or atheromatous plaque, and may be relatively soft (fresh) or may be in advance stages of atherosclerosis and hardened. The present invention uses an electrode array including a plurality of independently controlled electrodes distributed over the distal portion of a catheter to apply heat selectively to the stenotic material while limiting the unwanted heating of the blood and/or surrounding vessel wall. Since the atheromatous mass in the occluded blood vessel is preferentially heated and softened relative to the vessel wall, the path of the advancing catheter tip will be naturally confined in the lumen, away from the blood vessel wall. The electrode array will usually include at least two electrode terminals, more usually at least 20 electrode terminals, and preferably at least 36 electrode terminals, or more. As a result, the stenotic material is selectively softened, or weakened, permitting advancement of the catheter to recanalize the blood vessel lumen. Accordingly, this invention provides a method and apparatus for effectively penetrating a partially or totally occluded blood vessel by simultaneously applying both (1) heat to the stenotic material surrounding the tip of the catheter and (2) pressure against the heated stenotic material using the catheter itself. Optionally, subsequent recanalization procedures may be performed using either the same or a different catheter.

The present invention includes a means for guiding the catheter along a pathway approximating the central region of the occluded blood vessel. The guiding means is usually an electrically conducting wire that contains or serves as a common electrode for the heating means. The guiding means is extensible from the tip of the catheter and is located within and concentric to the catheter conveniently being in the form of a movable or fixed guidewire, usually being a movable guidewire. The electrode array is disposed proximally to the common electrode and positioned on or near the tip of the catheter.

Each individual electrode in this array is electrically insulated from all other electrodes in the array and is connected to its own power source or connection which limits or interrupts current flow to the electrode when low resistivity material (e.g. blood) causes a lower resistance path between the common electrode and the individual electrode. The tip of the catheter is thus composed of many independent electrode terminals designed to deliver electrical energy in the vicinity of the tip. The selective heating of the stenotic material is achieved by connecting each individual electrode terminal and the common electrode (e.g. on a guidewire) to an independent power source, which may be a substantially constant current power source. The application of high frequency voltage between the common electrode and the electrode array results in the conduction of high frequency current from each individual electrode terminal to the said common electrode. The current flow from each individual electrode terminal to the common electrode is controlled by either active or passive means, or a combination thereof, to selectively heat the stenotic material while minimizing the undesirable heating of the blood or the vessel wall.

This invention takes advantage of the differences in electrical resistivity between the stenotic material (atheromatous mass), blood, and blood vessel wall. By way of example, for any selected level of applied voltage, if the electrical conduction path between the common electrode (e.g. guidewire) and one of the individual electrode terminals within the electrode array is blood or blood vessel wall (each having a relatively low electrical resistivity), said current control means connected to individual electrode will limit current flow so that the heating of intervening blood or blood vessel wall is minimized. In contrast, if the electrical conduction path between the common electrode and one of the individual electrode terminals within the electrode array is atheromatous mass (having a relatively higher electrical resistivity), said current control means connected to said individual electrode will allow current flow sufficient for the heating and subsequent thermal softening or weakening of the intermediate atheromatous mass.

The application of a high frequency voltage between the common electrode and the electrode array for appropriate intervals of time substantially weakens the selectively heated atheromatous mass, allowing the catheter to penetrate and pass through the obstruction, thus recanalizing the blood vessel. Once the partially or fully occluded blood vessel has been opened to allow passage of the catheter, the catheter can be advanced to position a dilatation balloon (or other interventional or diagnostic element) within the occluding material. The dilatation balloon can then be used for angioplasty treatment in a substantially conventional manner.

Direct (Joulian) heating of the stenotic material by conduction of high frequency current softens the material over a distributed region. The volume of this distributed region is precisely controlled by the geometrical separation between the common electrode (e.g. the guidewire) and the electrode array. The rate of heating of the stenotic material is controlled by the applied voltage level. The use of high frequency current for Joulian heating also minimizes induced stimulation of muscle tissue or nerve tissue in the vicinity of the mass being heated. In addition, high frequencies minimize the risk of interfering with the natural pacing of the heart in circumstances where the catheter of the present invention is used in the coronary arteries.

The power applied to the common electrode and the electrode array will be at high frequency, typically between about 50 kHz and 2 MHz, usually being between about 100 kHz and 1 MHz, and preferably being between about 200 kHz and 400 kHz. The voltage applied will usually be in the range from about two volts to 100 volts, preferably being in the range from about five volts to 90 volts, and more preferably being in the range from about seven volts to 70 volts. Usually, the voltage applied will be adjustable, frequently in response to a temperature controller which maintains a desired temperature at the interface between the electrode array and the stenotic material. The desired temperature at the interface between the electrode array and the stenotic material will usually be in the range from about 38° C. to 100° C., more usually from about 38° C. to 80° C., and preferably from about 40° C. to 70° C.

A particular advantage of the present invention is that the heating means can be configured to a wide range of catheter sizes appropriate to the particular size of the occluded blood vessel or other body lumen or cavity being recanalized, typically in the range of diameters from 0.04 to 0.4 inches. The present invention can also incorporate a guidewire which can function as both a means for controlling and guiding the path of the catheter in the conventional manner, as well as to concentrate the thermal power density dissipated directly into the stenotic material by serving as the common electrode.

The preferred power source of the present invention can deliver a high frequency voltage selectable to generate power levels ranging from several milliwatts to 50 watts, depending on the size of the stenotic material being heated, the size of the blood vessel being recanalized, and the rate of advancement of the heating means through the stenotic material. The power source allows the user to select the voltage level according to the specific requirements of a particular angioplasty or other procedure.

The power source will be current limited or otherwise controlled so that undesired heating of blood, blood vessel wall, and other low electrical resistance materials does not occur. In the exemplary embodiment described below, current limiting resistors are placed in series with each independent electrode, where the resistor is 'sized' to provide an at least equal, and preferably greater, resistance than would normally be provided by the stenotic material. Thus, the electrode sees a substantially constant current source so that power dissipation through a low resistance path, e.g. blood, will be substantially diminished.

As an alternative to the current limiting resistors, a controlled power supply may be provided which interrupts the current flow to an individual electrode in the array when the resistance between that electrode and the common electrode falls below a threshold level. The control could be implemented by placing a switch in series with each electrode, where the switch is turned on and off based on the sensed current flow through the electrode, i.e. when the current flow exceeds a preselected limit, the switch would be turned off. The current limit could be selectable by the user and preferably would be preset at the time of manufacture of the power source. Current flow could be periodically sensed and reestablished when the stenotic material resistance is again present. Particular control system designs for implementing this strategy are well within the skill in the art.

Figure 1:
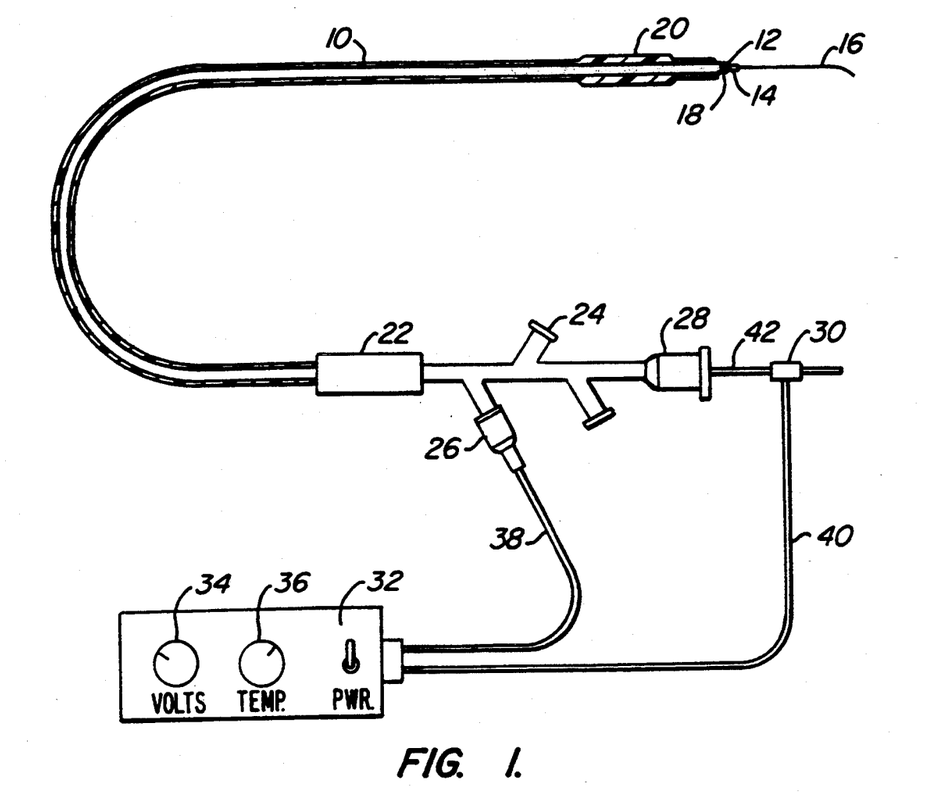
FIG. 1 is a perspective view of a catheter system constructed in accordance with the principles of the present invention, where the catheter includes a dilatation balloon.
Figure 2:
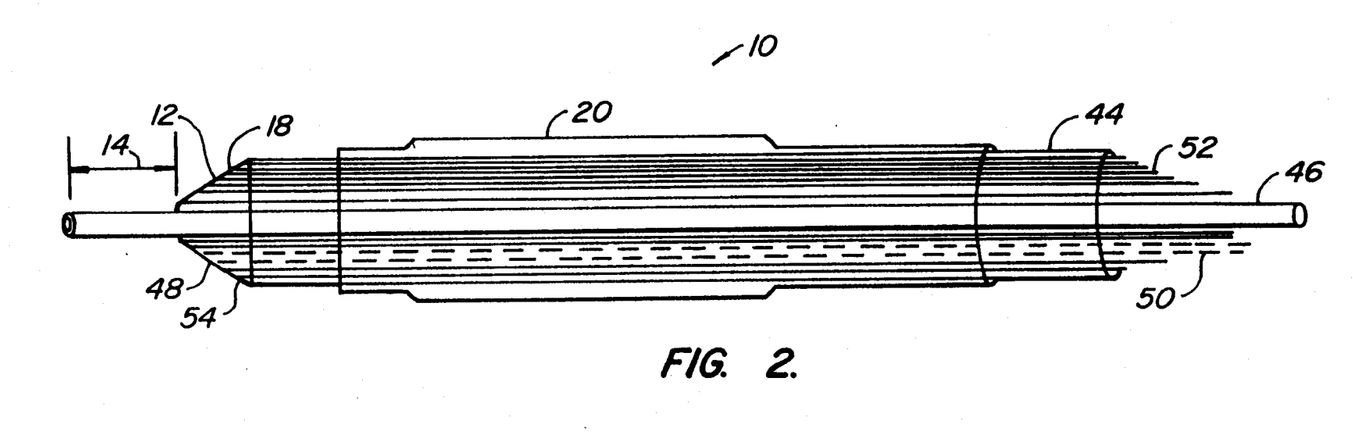
FIG. 2 is an enlarged view of the distal end of the catheter of FIG. 1, shown in section.

In an exemplary embodiment as shown in FIG. 1, a catheter 10 includes a guidewire 16 which functions both as a means for guiding the catheter into the intended position, as well as a common electrode. The entire guidewire may be an electrode, or it may contain an electrode. Referring to FIGS. 1 and 2, the catheter 10 also includes an array of electrode terminals 18 disposed on the distal tip 12 of the catheter 10. The electrode terminals 18 are electrically isolated from each other and from the common electrode 16. Proximally from the tip 12, the catheter 10 includes a conventional dilatation (angioplasty) balloon 20 generally concentric with the shaft of the catheter 10. Still referring to FIGS. 1 and 2, each of the terminals 18 is connected to the impedance matching network 22 by means of the individually insulated conductors 52. The proximal portion of the catheter 10 is also equipped with the fluid port 24 communicating with balloon 20. The guidewire is axially movable in an electrically insulating guidewire lumen tube 46, said lumen tube 46 being contained in, and concentric to, the catheter 10. The proximal end 42 of the guidewire is sealed against fluid leaks by a fluid seal 28. The proximal portion of the catheter 10 also has a connector 26 for providing the electrical connections to the matching network 22.

A power source 32 provides a high frequency voltage to the electrode terminals 18 by means of a cable 38 connectable to the connector 26. The power source 32 has a controller 34 to change the applied voltage level as well as a selector 36 for selection of the highest temperature at the tip 12 of the catheter 10 during its use, as explained later. Finally, the proximal portion of the guidewire electrode 42 is connected to the power source 32 by a detachable connector 30 and cable 40.

Figure 3:
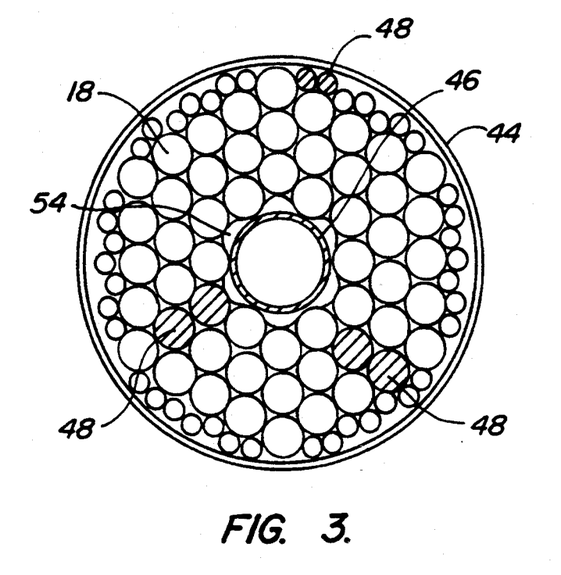
FIG. 3 is an end view of the distal tip of the catheter of FIGS. 1 and 2.

In the embodiment shown in FIGS. 1, 2, and 3, temperature sensors 48 are provided in the distal tip 12 of the catheter 10, typically thermocouple pairs (e.g. chromel and alumel). Said temperature sensors 48 and connected to the power source 32 by thermocouple wires 50 extending the length of the catheter 10 and by the cable 38 connected through the connector 26. The temperature sensors 48 at the tip 12 of the catheter 10 are connected to a feedback control system in power source 32 to adjust the power output so that the user selectable temperature is not exceeded during the use of the catheter in recanalization of an occluded blood vessel. Power output could be controlled by any conventional technique, such as control of voltage, current, duty cycle, or the like. The selectable temperature is selected by the user by adjusting selector 36 provided in the power source 32.

Referring to FIG. 2, the distal tip 12 of the catheter 10 of the preferred embodiment contains the exposed terminals of the electrode terminals 18 and the temperature sensors 48. The terminals 18 and temperature sensors 48 are secured in a matrix of suitable insulating material (e.g. epoxy) 54 and formed in a generally tapered or hemispherical shape, preferably being a conical or "nose cone" configuration. Proximal to the tapered tip 12, the temperature sensor wires 50 and electrode wires 52 are contained in a jacket 44 of cylindrical shape covering the length of the catheter 10.

An end view of the catheter 10 at the tip 12 is illustrated in FIG. 3. Referring to FIGS. 2 and 3, electrode terminals 18 are electrically insulated from each other and from temperature sensors 48, and are secured together in a bundle by the electrically insulating material 54. Proximal to the tip 12, the thermocouple wires 50 and electrode wires 52 are contained in a suitable jacket 44 of cylindrical shape covering the length of the catheter 10. The central portion of the catheter 10 contains the electrically insulating guidewire lumen tube 46 which provides a lumen for the guidewire 16. The distal end of the said tube 46 optionally extends beyond the tip 12 to provide a tip offset 14. The intended purpose of said tip offset 14 is to provide a minimum separation between the said common electrode on guidewire 16 and array of electrodes 18, usually being at least 0.02 inches, more usually being at least 0.15 inches, and sometimes being 0.25 inches or greater.

Figure 4:
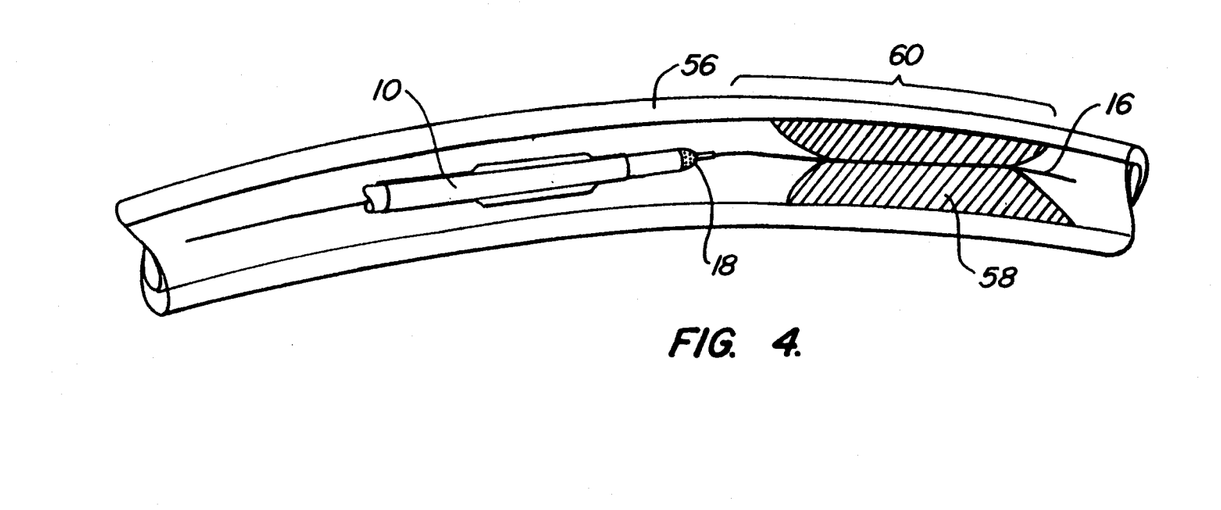
FIGS. 4–8 illustrate the use of the catheter of FIGS. 1–3 in the recanalization of a stenosed region within a blood vessel according to the method of the present invention.

FIG. 4 illustrates how the catheter 10 can be applied to recanalize a blood vessel 56 occluded with an atheromatous plaque 58. In this case, the guidewire 16 is first advanced to the site of the atheromatous plaque 58, and the catheter 10 is then moved over the guidewire 16 to contact a leading edge of the plaque. Next, the guidewire 16 is advanced through the plaque 58 under fluoroscopic guidance, exposing a length 60 of the guidewire which is electrically conducting.

Figure 5:
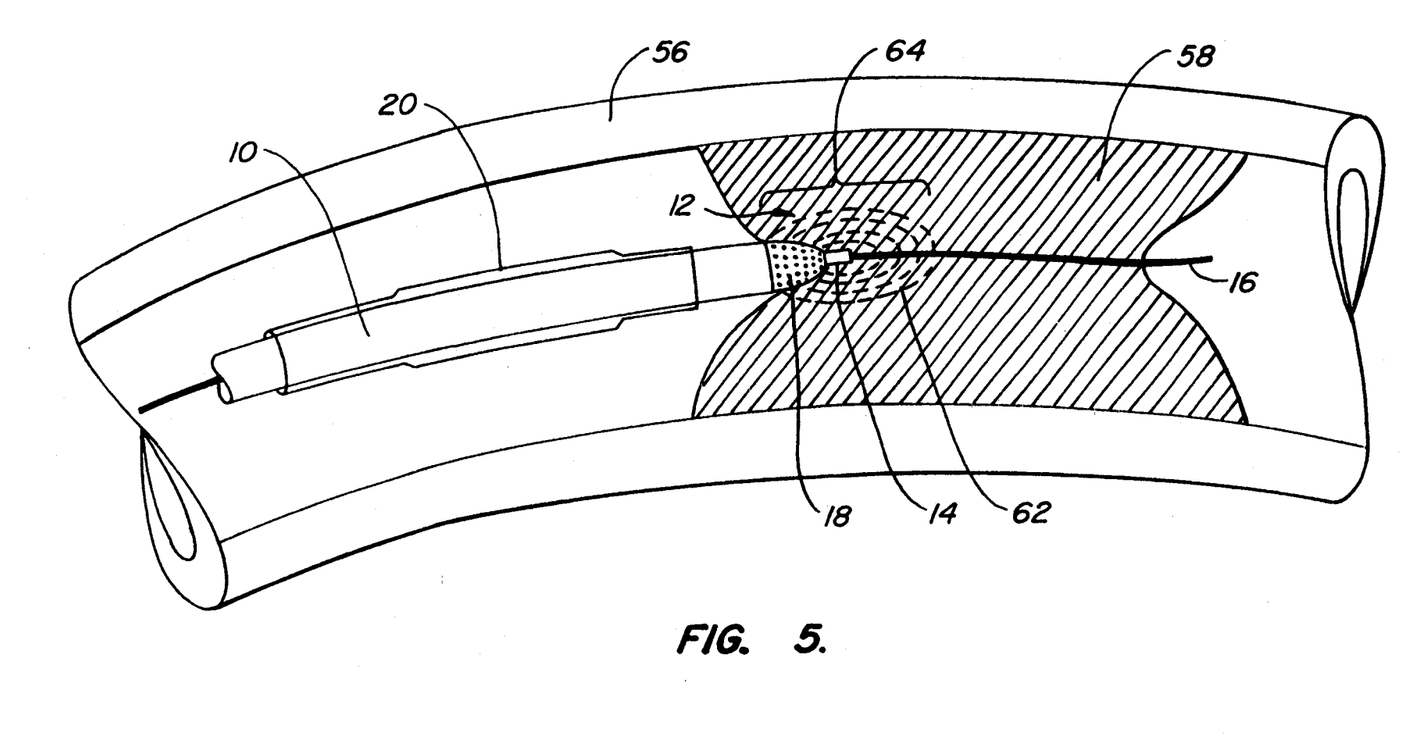

Referring next to FIG. 5, the distal tip 12 of the catheter 10 comprising the array of electrode terminals 18 is urged against the atheromatous plaque 58. A high frequency voltage is applied between the common electrode on guidewire 16 and each of the electrode terminals 18. The resulting electrical current flows between the said common electrode 16 and the electrode terminals 18 through the atheromatous plaque 58, as illustrated by current flux lines 62. Due to the electrical resistance of the atheromatous plaque 58, the localized current flow heats the plaque 58 in a zone 64. The localized heating is adjusted by varying the level and duration of the high frequency voltage.

The tip offset 14 maintains a minimum distance between the electrode 18 and the common electrode (guidewire) 16. The zone of heating 64 within the plaque 58 is defined by the boundary of the current flux lines 62. The atheromatous plaque material softens in the heated zone 64, which facilitate the forward axial advancement of the catheter tip 12 through said heated zone. Said movement of the tip 12 effects the displacement of the plaque material, thereby recanalizing (creating an opening through) the previously occluded blood vessel 56. The catheter 10 is advanced through the softened plaque until a channel is created in the occluding mass. The catheter 10 is withdrawn leaving a vessel recanalized allowing an improved flow of blood therethrough.

After the catheter 10 has been advanced through the heated plaque, if necessary, the balloon 20 can be inflated with appropriate fluid to appropriate pressures to effect conventional angioplasty.

Figure 6:
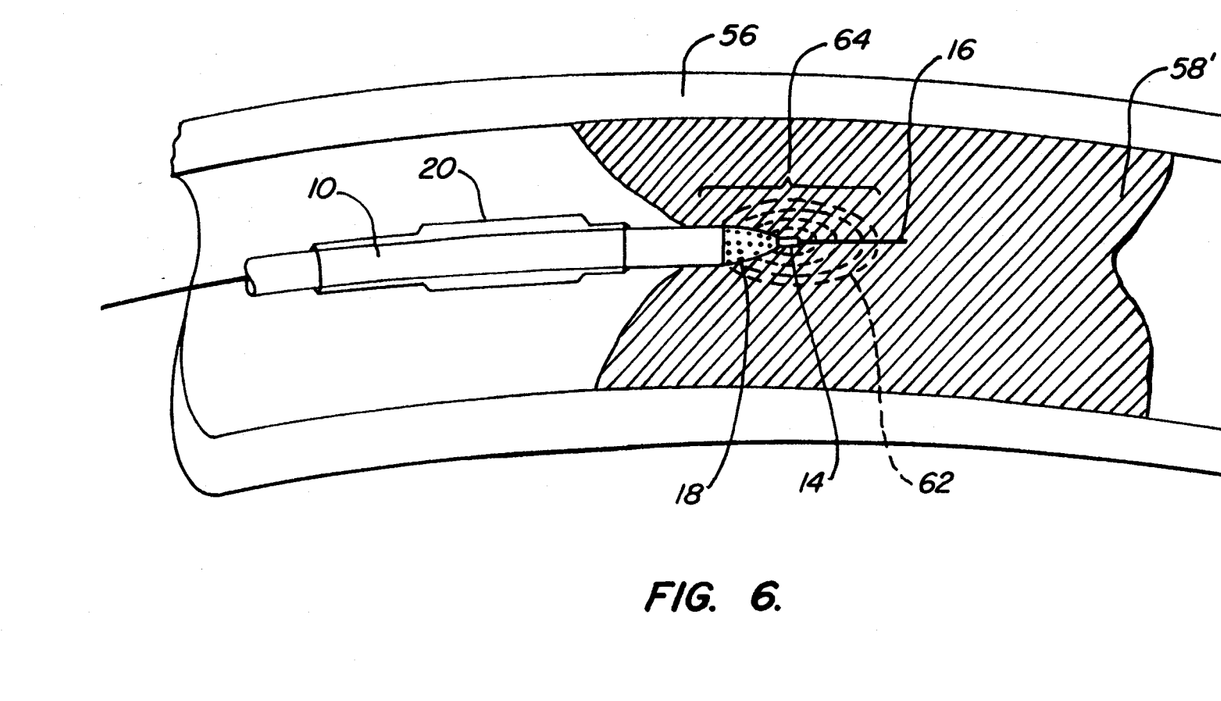

There are situations where a guidewire cannot be completely advanced across a stenosed region 58, as illustrated in FIG. 6. In such cases, the common electrode (guidewire) 16 is partially penetrated into the atheromatous plaque 58' to the extent possible. The array of electrodes 18 is contacted against the wall of plaque 58', and the tip offset 14 creates a minimum spacing between the common electrode 16 and the electrode array so that some heating of plaque will occur. The catheter 10 and the common electrode 16 can then be alternately advanced until a channel is created through the entire region of plaque 58'. Once again, conventional balloon angioplasty can be performed once the balloon 20, in its deflated position, has been advanced across the plaque 58'.

Figure 7:
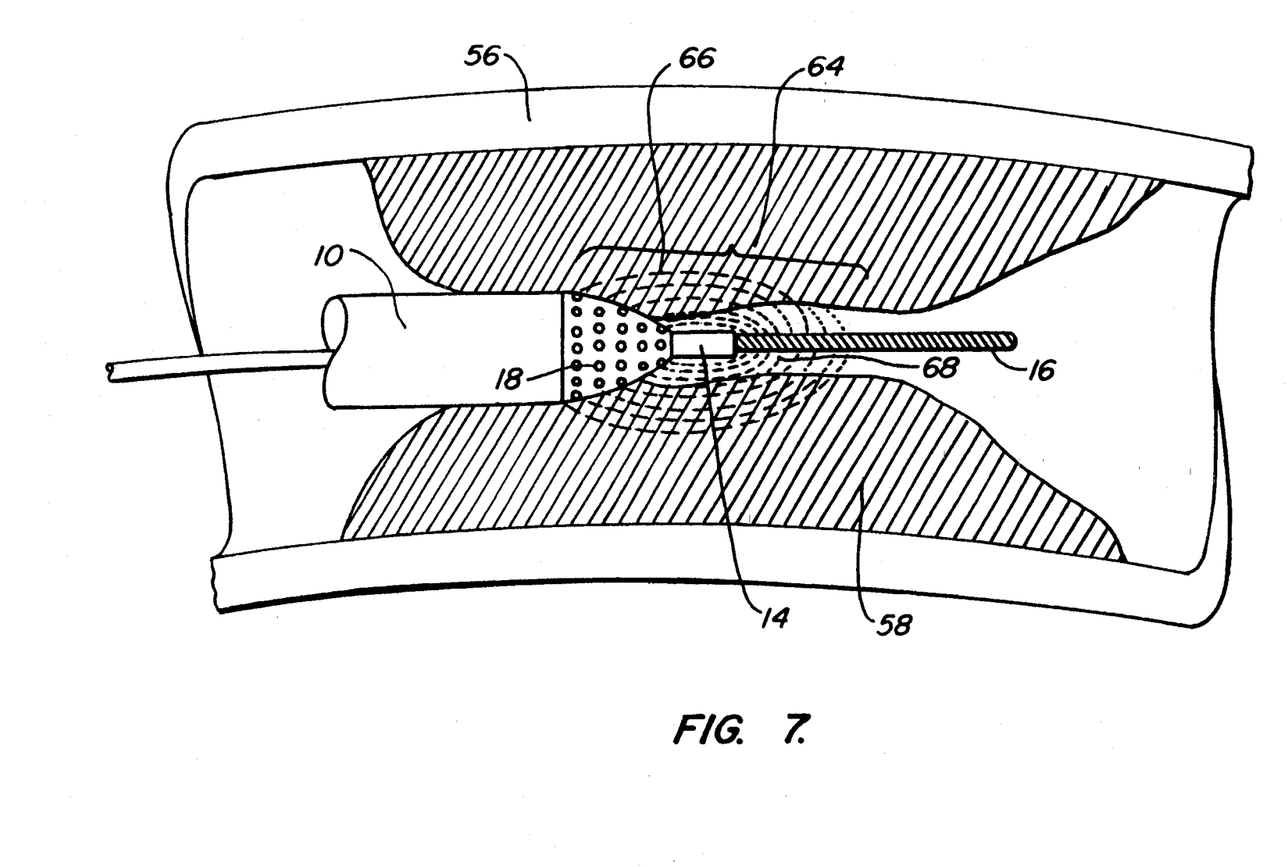
Figure 8:
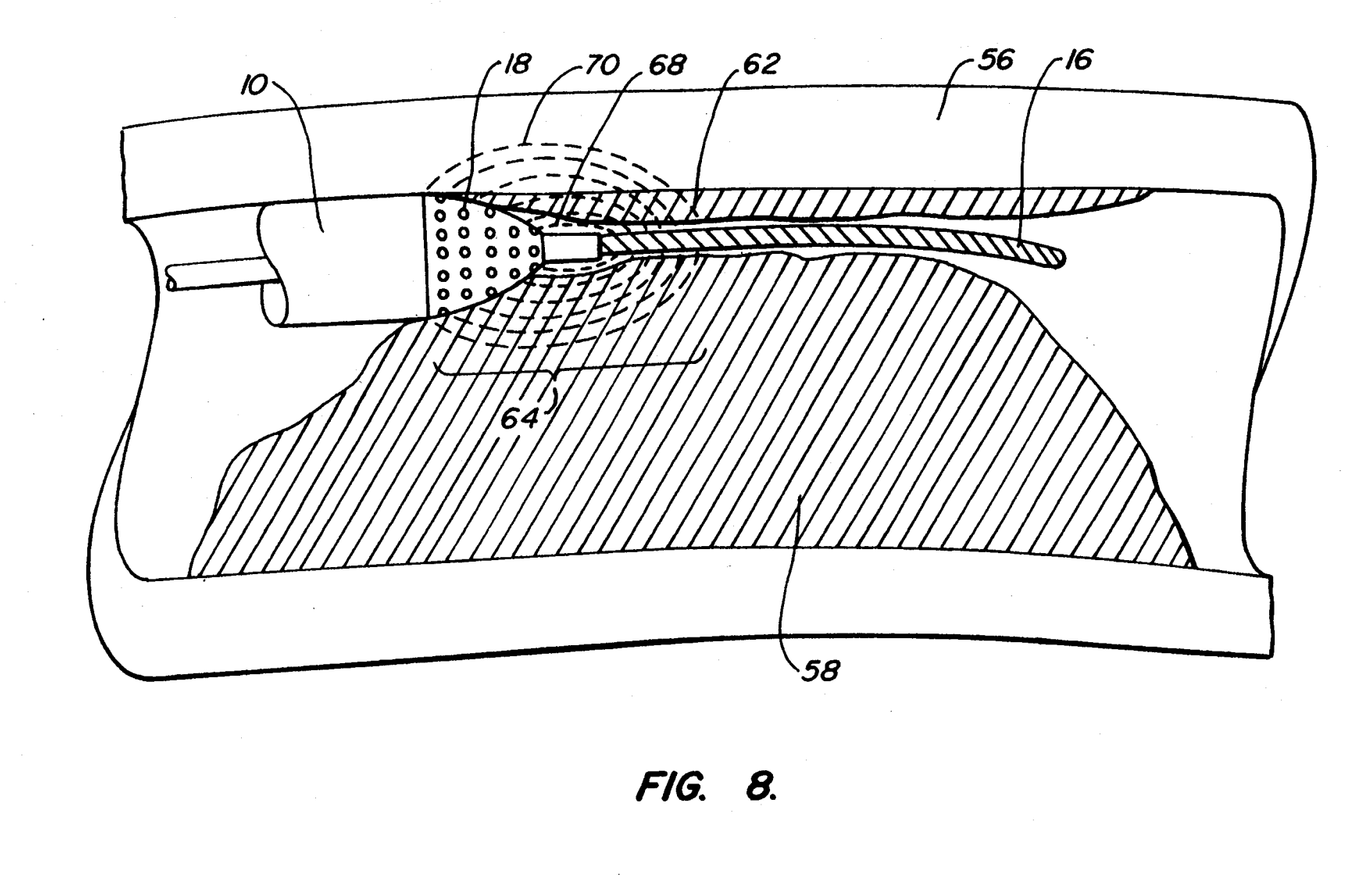

A central aspect of the present invention is the ability of the catheter 10 to deliver electrical energy effectively only to the intended areas, i.e. the atheromatous material, and not to the blood or the blood vessel. Such directed energy transfer results in selective heating of the atheromatous material which allows the catheter to be "self-guiding" as described above. When the tip 12 of the catheter 10 is pressed against a region of stenotic material, some of the electrode terminals 18 will be in contact with atheroma, while other electrode terminals may be in contact with blood, and yet others may be in contact with the blood vessel wall. These situations are illustrated in FIGS. 7 and 8. Each of the electrode terminals 18 experiences an electrical impedance which is characteristic of the material which is disposed between the individual electrode terminal and the common electrode. The present invention takes advantage of the fact that the electrical resistivity of typical atheroma is higher than that of blood or blood vessel wall. Thus, if the current passing through each of the electrode terminals 18 is limited to a substantially constant value, the regions of higher electrical resistivity will generate more Joulian heating (power=$I^2R$, where I is the current through resistance R) than a region of lower electrical resistivity. Therefore, the atheromatous plaque of the stenotic region will be selectively heated up while the blood and blood vessel wall will experience a minimal rise in temperature. Thus, the catheter will selectively advance through the atheroma which has been heated and softened.

The heating selectivity of the present invention is accomplished by selecting the electrical resistance of the various components which comprise the pathway of the electrical current 62 between the common electrode (guidewire) 16 and each of the electrode terminals 18 in the electrode array located at the tip 12 of the catheter 10. By way of example, the electrical resistivity of blood at body temperature is in the range from 148 to 176 Ohm-cm at a frequency up to 120 kHz (Geddes et al. (1967) Med. Biol. Eng. 5:271-293). The electrical resistivity of human cardiac and skeletal muscle (which approximates the structure of the blood vessel wall) is in the range of 100 to 456 Ohm-cm at frequencies in the range 100 to 1000 kHz. (Geddes et al. (1967), supra).

In contrast, atheromatous mass generally resembles fat-like deposits and contains cholesterol, lipids, and lipidophages. Based on its primarily fat-like composition, the atheromatous mass has a relatively high electrical resistivity as compared with blood. The electrical resistivity of fat-like substances in human has been reported in the range of 1,000 to 3,000 Ohm-cm at frequencies ranging from 100 to 1,000 kHz (Geddes et al., (1967), supra). This invention utilizes the inherent two to ten fold difference in electrical resistivities to selectively heat the atheromatous plaque in a blood vessel.

Figure 9:
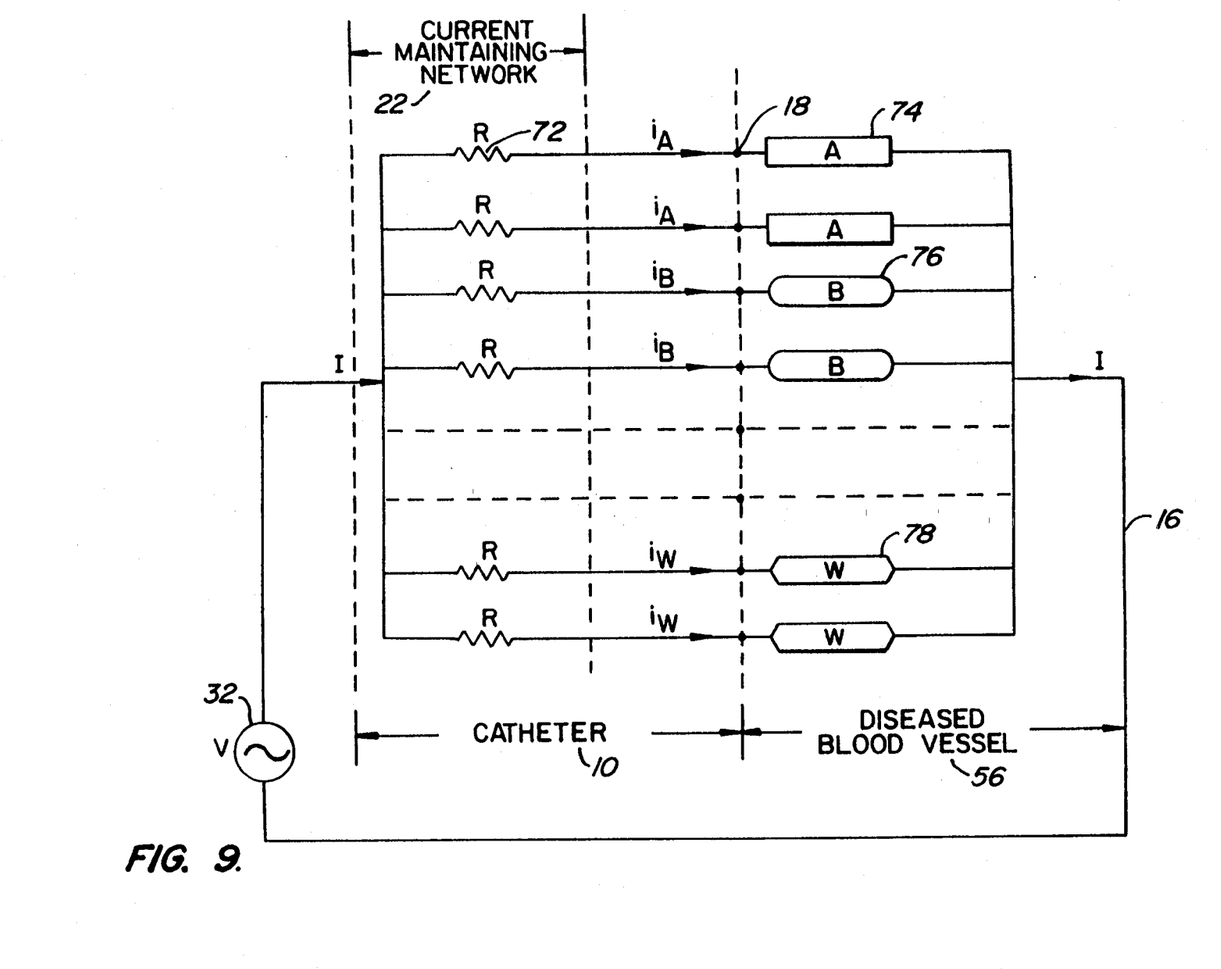
FIG. 9 is a schematic illustration of a current limiting power supply useful as part of the catheter system of the present invention.

Each of the electrode terminals 18 is connected to an individual source of current by means of wires 52. A current limiting network providing the controlled or constant current, as described above, is contained in a junction box 22. The network can be composed of either active or passive electronic components to perform its intended function. By way of example, and not intending to limit the scope and spirit of this invention, a network composed of passive circuit elements, i.e. resistors, is illustrated in FIG. 9. Referring to FIGS. 1, 2, and 9, a constant current network 22 consists of a multiplicity of resistors 72 which are same in number as the electrode terminals 18. Each resistor is connected between a power source 32 (by the connector 26 and cable 38) and the corresponding electrode terminal 18 (by wire 52). The current will be maintained substantially constant so long as each resistor impedance is sufficiently higher than the load impedance. Suitable resistor values will be in the range from 500Ω to 50,000Ω, usually being in the range from 1,000Ω to 25,000Ω, preferably being in the range from 3,000Ω to 15,000Ω.

Still referring to FIGS. 1 and 9, each electrode terminal 18 is connected to a load represented by the atheroma, blood, or blood vessel wall. More specifically, the load impedance 74 of the atheroma is designated by A, the load impedance 76 of blood is denoted by B, and load impedance 78 of vessel wall is denoted by W respectively. As the current passes through these components, it is received by the common electrode (guidewire) 16 which is in turn connected to the power source 32 by connector 30 and cable 40. The level of the current flowing in the circuits is controlled by the voltage applied between the proximal end of the resistor network 22 and the common electrode (guidewire) 16.

The expected power delivered to each of the loads (i.e. atheroma, blood, and vessel wall tissue) can be calculated based on exemplary values for the different parameters as enumerated below:

| | |
|---|---|
| Catheter diameter (5 French), D | 1.66 mm |
| Number of Electrodes Terminals 18, n | 60 |
| Size of the electrode 18 tip, d | 0.004" dia. |
| Resistance of the network resistor 72, R | 10,000 Ohms |
| Impedance 74 of atheroma, A | 3,000 Ohms |
| Impedance 76 of blood, B | 200 Ohms |
| Impedance 78 of vessel wall, W | 500 Ohms |
| Applied voltage from source 32 W: | 40 Volts, RMS |

Calculated power dissipation per electrode in:

| | |
|---|---|
| Atheroma | 28 milliwatts |
| Blood | 3 milliwatts |
| Vessel Wall | 7 milliwatts |

Calculating power ($I^2R$) from the above, the power dissipation in the atheromatous plaque is approximately ten times that in blood and four times that in blood vessel wall respectively. Taking into account the heat capacities of various components, the expected temperature in the atheromatous plaque will be considerably greater than in the blood or blood vessel wall.

The desired temperature rise of the atheromatous plaque to effect desired recanalization is of the order of 10° to 60°. Based on the above calculation, a 10° to 60° C. increase in the temperature of the atheromatous plaque using the apparatus and method of the present invention will result in a corresponding rise of blood temperature in the range of 1° C. to 6° C. caused by the current flowing directly through the blood.

Once a sufficient temperature rise is accomplished in the atheromatous plaque, the mechanical strength of the said mass is substantially reduced in the localized region surrounding the tip 12 of the catheter 10. This allows the catheter 10 to be advanced incrementally through the plaque by applying a longitudinal force on the portions of the catheter 10 external to the patient. This force is transmitted along the length of the catheter 10 to the tip region 12 to create a "boring pressure" sufficient to penetrate the plaque 58. As the blood vessel wall is not equivalently heated or softened, the catheter will preferentially advance through the plaque 58 following a path of its own creation.

The method of controlling the heating by the thermally assisted angioplasty catheter of this invention can also be accomplished by temperature feedback control mechanism. The temperature of the atheroma in contact with the tip 12 is sensed by temperature sensing elements such as means of thermocouple pairs (FIG. 3) 48. A feedback control loop contained in the power source 32 allows the adjustment of the necessary voltage applied so that the required temperature rise in the atheroma is accomplished. Conversely, by continuously monitoring the temperature of the atheroma being heated, the appropriate voltage level is continuously maintained such that the user-selected temperature is never exceeded.

While the above description provides a full and complete disclosure of a preferred embodiment of the invention, various modifications, alternative constructions, and equivalents may be employed. For example, the power could be communicated to the electrodes by wires imbedded in the catheter wall. Also, the temperature sensing may be achieved using fiber optics with infrared sensing technique, a thermocouple, a thermistor or other temperature sensing means. Alternatively, by proper selection of metals used for (1) multiplicity of electrodes and leads (e.g. Constantan) and (2) guidewire (e.g. steel), each individual electrode can function as a thermocouple in conjunction with the singular guidewire. The measurement of the direct current voltage between the guidewire and the multiplicity of electrodes indicates the maximum temperature which occurs at any location on the catheter tip. This information can then be used in the feedback control loop as described above to assure an improved safe upper limit on the operating temperature during the use of the apparatus of the present invention.

Figure 10:
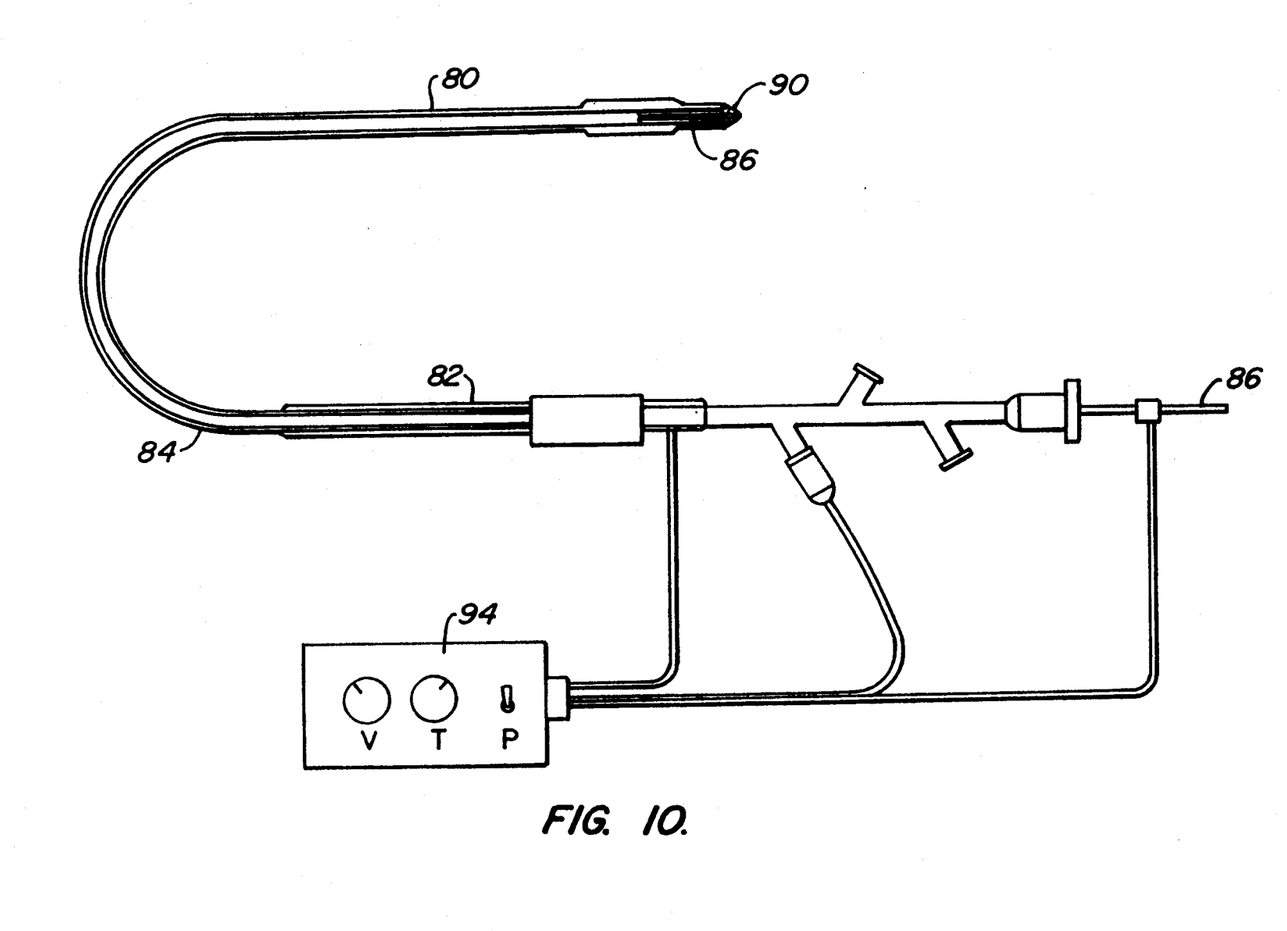
FIG. 10 is a second embodiment of a catheter system constructed in accordance with the principles of the present invention.

A more preferred embodiment of the catheter of this invention is shown in FIG. 10. In this embodiment, the catheter 80 is substantially similar in construction to that of FIG. 1, except that a second electrode 82 is provided for on the body 84 of the catheter shaft instead of the guidewire being the second electrode. During use of the catheter 80 in therapy, this second electrode 82 is intended to be in electrical contact with the blood in the artery. The location of the second electrode 82 is shown to be near the proximal end of the catheter 80, but could also be disposed more distally.

Still referring to FIG. 10, guidewire 86 is connected to the current-limiting circuitry in power source 94 in a manner similar to the electrical connection of tip electrodes 90. During use of the catheter 80, the guidewire 86 becomes an additional electrode working in conjunction with the other tip electrodes. In this embodiment, no offset between the guidewire 86 and the electrode array 90 is required.

Figure 11:
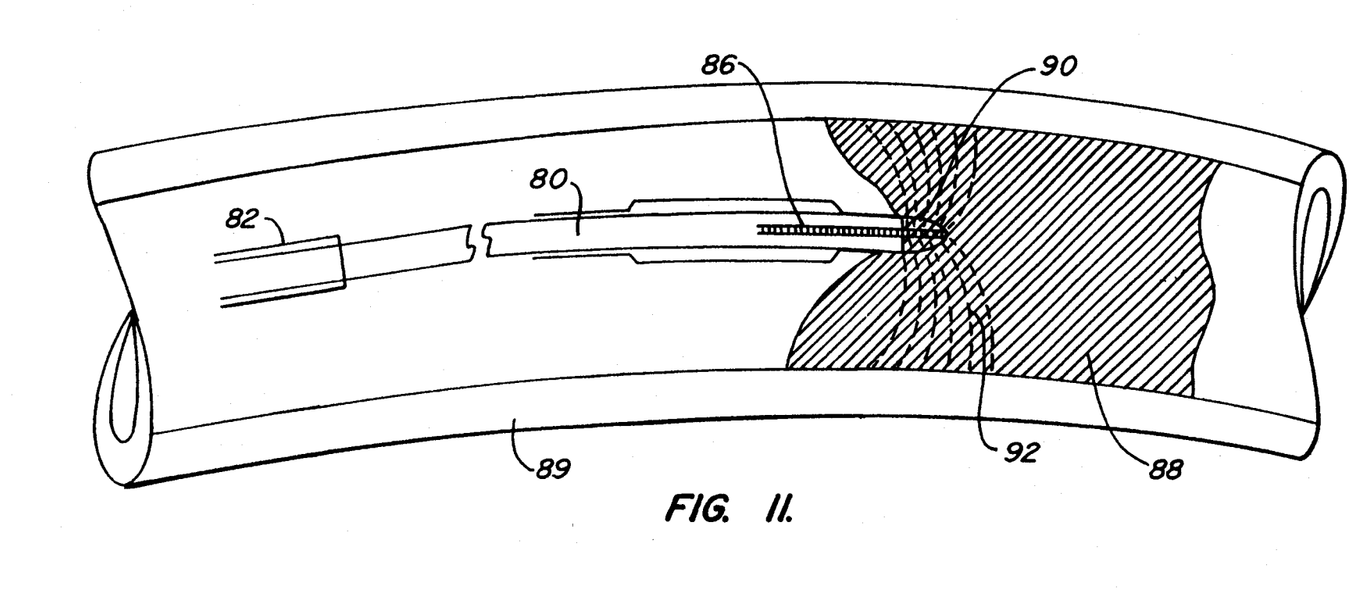
FIG. 11 illustrates use of the catheter of FIG. 10 in the recanalization of a stenosed region within a blood vessel according to the method of the present invention.

Referring now to FIG. 11, the catheter 80 is advanced over the guidewire 86 to the site of a total occlusion 88 in the artery 89. The electrode array 90 and the guidewire 86 are connected to the power source 94 (FIG. 10), and the second electrode 82 is connected to an opposite polarity terminal of the power source. By applying power to the electrodes 90 and 82, current flux lines 92 are formed and distributed in the occlusion 88. The highest current density exists at the immediate vicinity of the tip electrode array 90, thereby producing maximum heating of the atheroma in contact with the catheter tip. A return path for the electrical current from the tip electrodes 90 to the second electrode 82 is defined through the blood in the blood vessel, the blood vessel wall, and/or the surrounding tissue. However, the current is most likely to flow through the blood and blood vessel wall as these components have much lower resistivity as compared to other body tissue. The second electrode 82 is designed to be long with a large surface area to ensure low density of current flux lines at said second electrode.

As the current passes through, the temperature of the occluding material 88 is raised, thereby softening the occlusion. The catheter 80 along the guidewire 86 is advanced through this softened atheroma until the vessel is recanalized. A final recanalization step can then be performed by balloon dilatation or other currently available therapeutic techniques.

Figure 12:
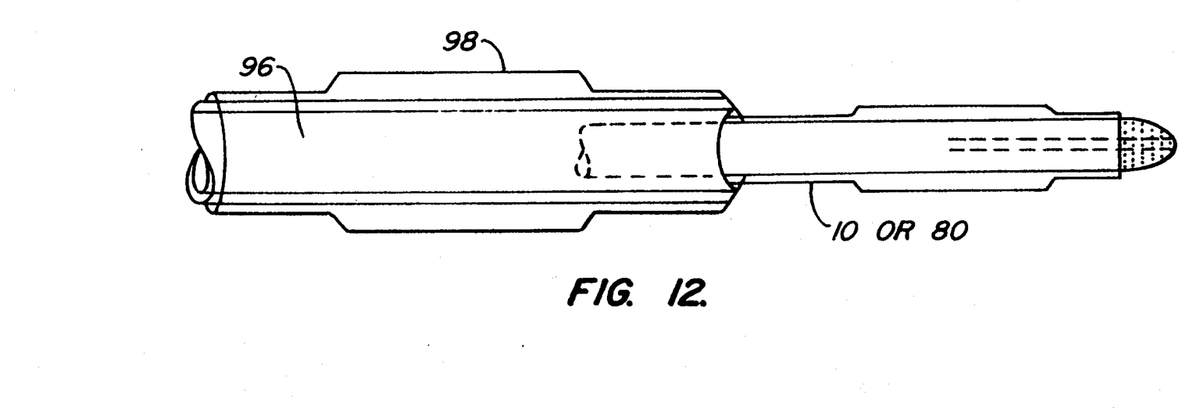
FIG. 12 illustrates a third embodiment of a catheter constructed in accordance with the principles of the present invention in combination with an anchoring catheter sheath.

It is understood that the plaque in the total occlusions can be dense and somewhat hard to push a catheter through even though it is heated. In order to facilitate the mechanical advancement of the catheter through the plaque, another embodiment of the catheter system of the present invention is illustrated in FIG. 12. The catheter 10 of FIG. 1 or catheter 80 of FIG. 10 is placed in a sheath catheter 96. The distal end of the sheath catheter 96 includes one or a plurality of expanding means 98, such as inflatable balloons. The proximal end of the sheath catheter 96 includes the necessary blood scaling means and balloon expanding ports. The shaft of the sheath catheter 96 includes the necessary lumen(s) for expanding said balloon(s) 98.

Figure 13:
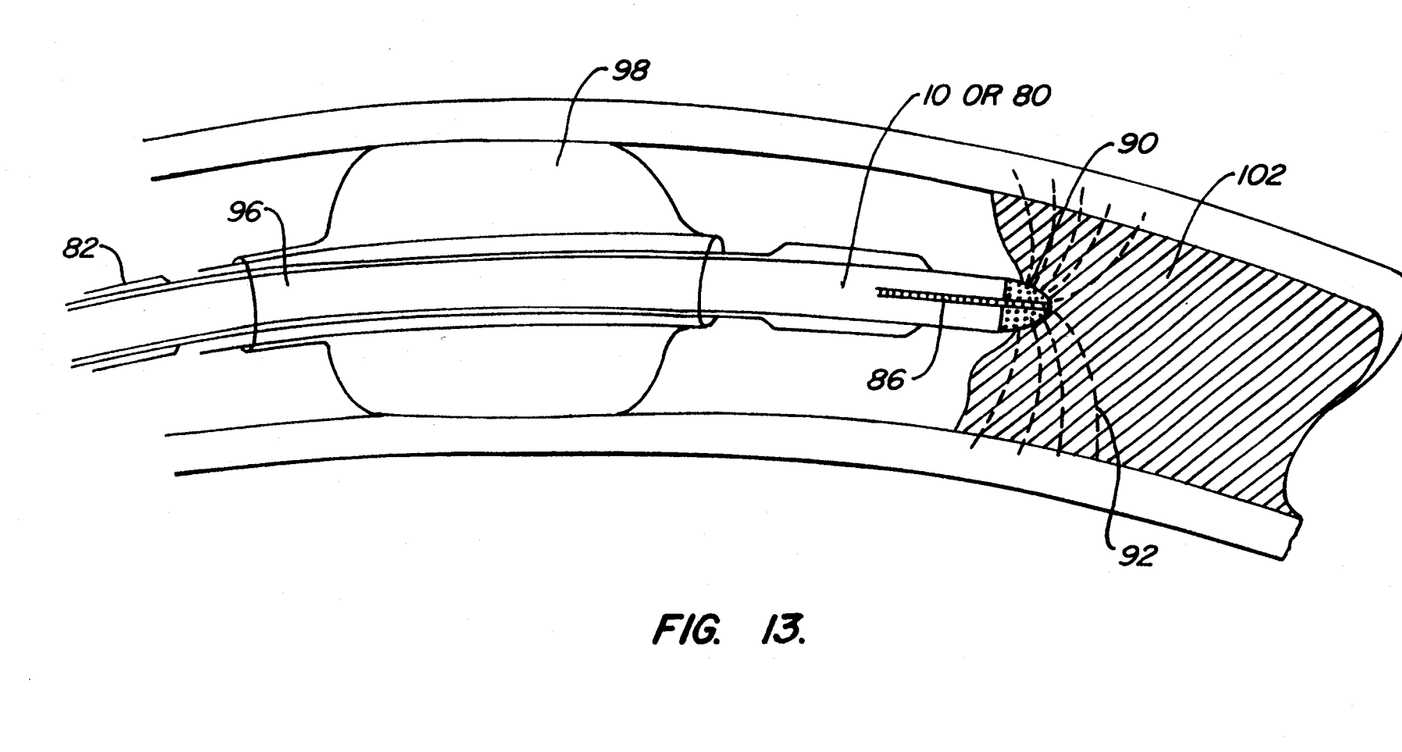
FIG. 13 illustrates the use of the catheter and catheter sheath of FIG. 12 in the recanalization of a stenosed region within a blood vessel according to the method of the present invention.

The purpose of the sheath catheter 96 is to provide an anchor for the main catheter 10 or 80 while in use. Specifically referring to FIG. 13, the catheter system (comprising of the sheath catheter 96 and the main catheter 10 or 80) is advanced to the site of the occlusion 102 (FIG. 11). The balloon(s) 98 are inflated and the sheath catheter 96 is thus anchored in position in the blood vessel proximate to the occlusion. The main catheter 10 or 80 is then advanced inside the sheath catheter 96 against the occlusion 102. The main catheter tip 90 is then energized, and further advanced through the softened atheroma. The sheath catheter 96 with inflated balloon(s) 98 thus serves as an anchoring means assisting in the advancing of the main catheter 10 or 80 through the occlusion 102.

Although the foregoing invention has been described in detail for purposes of clarity of understanding, it will be obvious that certain modifications may be practiced within the scope of the appended claims.

What is claimed is:

1. A catheter system comprising:

a catheter body having a proximal end and a distal end;

an electrode array disposed near the distal end of the catheter body, said array including a plurality of electrically isolated electrode terminals disposed over a contact surface which is forwardly disposed to contact an occluding surface in a body lumen as the catheter is advanced through the lumen;

a common electrode; and means for supplying high frequency power to said electrode array, wherein current flow to each individual electrode terminal is selectively limited or disrupted when a low resistance path exists between said electrode terminal and the common electrode.

2. A catheter system as in claim 1, wherein the common electrode is disposed on the catheter body proximally of the electrode array.

3. A catheter system as in claim 1, wherein the common electrode comprises a wire extending distally from the catheter body.

4. A catheter system as in claim 1, wherein the common electrode comprises means for external attachment to a patient's body.

5. A catheter system as in claim 1, further comprising an interventional element disposed proximally of the electrode array on the catheter body.

6. A catheter system as in claim 5, wherein the interventional element comprises a dilatation balloon.

7. A catheter system as in claim 1, further comprising means for measuring temperature disposed near the distal end of the catheter body.

8. A catheter system as in claim 7, wherein the means for measuring temperature comprises a plurality of temperature sensing elements disposed within the electrode array.

9. A catheter system as in claim 7, whereby the means for applying the high frequency voltage comprises means for controlling the voltage based on the temperature sensed by the temperature sensing means.

10. A catheter system as in claim 1, further comprising means for individually limiting current flow through each electrode terminal in order to control current flow.

11. A catheter system as in claim 10, wherein the means for limiting current flow comprises a plurality of current limiting resistors located within the catheter body, with at least one resistor connected to each electrode terminal.

12. A catheter system as in claim 10, wherein the means for limiting current flow comprises a plurality of current limiting resistors located within the voltage applying means, with at least one resistor connected to each electrode terminal.

13. A catheter system as in claim 1, wherein the contact surface is a tapered surface at the distal end of the catheter body.

14. A catheter system as in claim 13, wherein the tapered surface is of nosecone configuration.

15. A catheter comprising:

a catheter body having a proximal end, a distal end, and a guidewire lumen;

an electrode array disposed near the distal end of the catheter body, said array including a plurality of isolated electrode terminals disposed over a tapered distal contact surface; and means at the proximal end of the catheter body for simultaneous connecting each individual isolated electrode terminal to a high frequency power supply.

16. A catheter as in claim 15, further comprising a plurality of current limiting resistors disposed in the catheter body, with at least one resistor connected in series between each electrode terminal and the power supply.

17. A catheter as in claim 15, wherein the means for connecting comprises a plurality of conductors disposed in the catheter body for connecting the resistors to the power supply.

18. A catheter as in claim 15, further comprising an interventional element disposed proximally of the electrode array on the catheter body.

19. A catheter as in claim 18, wherein the interventional element comprises a dilatation balloon.

20. A catheter as in claim 18, further comprising means for measuring temperature disposed near the distal end of the catheter body.

21. A catheter as in claim 20, wherein the means for measuring temperature comprises a plurality of temperature sensing elements distributed within the electrode array.

22. A catheter as in claim 15, further comprising a movable guidewire slidable disposed within the guidewire lumen, wherein said guidewire is electrically isolated from the electrode array and includes a common electrode and means for connecting the common electrode to a high frequency power supply.

23. A catheter as in claim 15, further comprising a common electrode disposed on the catheter body proximally of the electrode array.

24. A catheter as in claim 15, wherein the current limiting resistors have a resistance in the range from $500\Omega$ to $50,000\Omega$.

25. A catheter as in claim 15, wherein the electrode array includes at least 20 electrode terminals disposed over the tapered surface at the distal end of the catheter body.

26. A catheter as in claim 25, wherein the tapered surface is of nosecone configuration.

27. A catheter system comprising:

a catheter guide having a proximal end, a distal end, a lumen therethrough, and a common electrode disposed on an exterior distal surface;

a catheter body disposed within the lumen of the catheter guide, said catheter body having a proximal end, a distal end, and an electrode array disposed substantially uniformly over a contact surface at the distal end, said electrode array including a plurality of electrically isolated electrode terminals, wherein the contact surface is forwardly disposed to contact an occluding surface in a body lumen as the catheter is advanced through the body lumen; and means for individually connecting the electrode terminals to a high frequency power supply along isolated high impedance conductive paths:

whereby the common electrode and the electrode array may be connected to a high frequency power supply to efficiently deliver energy to a patient surface contacted by the electrode array and electrically exposed to the common electrode.

28. A catheter system as in claim 27, wherein the catheter guide comprises an inflatable balloon disposed near its distal end.

29. A catheter system as in claim 27, further comprising a guidewire received in a guidewire lumen in the catheter body, wherein the guidewire is electrically coupled to the electrode array.

30. A catheter system as in claim 27, wherein the means for connecting comprises a plurality of current limiting resistors connected in parallel between the individual electrode terminals and a common pole of the power supply.

31. A catheter systems as in claim 30, wherein the current limiting resistors are disposed in the distal end of the catheter body.

32. A catheter system as in claim 28, wherein the contact surface is tapered.

33. A catheter system as in claim 32, wherein the tapered surface is of nosecone configuration.

34. A method for applying energy to an occluding surface in a body lumen, said method comprising:

positioning a catheter within the body lumen so that an electrode array including a plurality of forwardly disposed isolated electrode terminals contacts the surface; and supplying high frequency power to said each of the electrode terminals in the electrode array, wherein current flow through each electrode terminal is individually controlled, wherein the surface is heated by the flow of current from individual electrode terminals which contact the surface and current flow from the terminals which do not contact the surface is limited or disrupted.

35. A method as in claim 34, wherein a common electrode is contacted against the patient as part of a guidewire.

36. A method as in claim 35, wherein the catheter is positioned over the guidewire.

37. A method as in claim 34, wherein a common electrode is contacted against the patient's skin.

38. A method as in claim 34, wherein a common electrode is disposed within the body lumen to form a conductive path through a fluid within the body lumen.

39. A method as in claim 34, wherein the high frequency voltage is in the range from 50 kHz to 2 MHz and the voltage is in the range from two volts to 100 volts.

40. A method as in claim 34, further comprising measuring temperature at an interface between the electrodes and the stenotic material.

41. A method as in claim 40, further comprising controlling the applied power based on the measured interface temperature.

42. A method as in claim 34, further comprising advancing an interventional element into the opening and treating the occluded region with the interventional element.

43. A method as in claim 42, wherein the interventional element is an expandable balloon on the catheter body and treating comprises expanding the balloon within the opening.

44. A catheter comprising:

a catheter body having a proximal end, a distal end, and a guidewire lumen;

an electrode array disposed near the distal end of the catheter body, said array including at least 20 isolated electrode terminals disposed over a distal contact surface;

means at the proximal end of the catheter body for simultaneously connecting each individual isolated electrode terminal to a high frequency power supply.

* * * * *